(12) United States Patent
Petersen et al.

(10) Patent No.: US 6,888,009 B2
(45) Date of Patent: *May 3, 2005

(54) METHOD FOR THE PREPARATION OF 5-CARBOXYPHTHALIDE

(75) Inventors: Hans Petersen, Vanløse (DK); Poul Dahlberg Nielsen, Vig (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/140,361

(22) Filed: May 6, 2002

(65) Prior Publication Data

US 2002/0165403 A1 Nov. 7, 2002

Related U.S. Application Data

(63) Continuation of application No. 09/690,301, filed on Oct. 17, 2000, now Pat. No. 6,458,973.

(30) Foreign Application Priority Data

Nov. 1, 1999 (DK) .......................... 1999 01569

(51) Int. Cl.$^7$ ............................................ C07D 307/77

(52) U.S. Cl. ..................................................... 549/305

(58) Field of Search ................................. 549/305, 467

(56) References Cited

U.S. PATENT DOCUMENTS

| | | | |
|---|---|---|---|
| 3,467,675 A | | 9/1969 | Peterson et al. ......... 260/346.2 |
| 3,607,884 A | * | 9/1971 | Forney ....................... 549/307 |
| 4,136,193 A | | 1/1979 | Bogeso et al. ............. 424/285 |
| 4,650,884 A | | 3/1987 | Bogeso ...................... 549/467 |
| 4,943,590 A | | 7/1990 | Boegesoe et al. .......... 415/469 |
| 5,296,507 A | | 3/1994 | Tanaka et al. ............. 514/465 |
| 6,020,501 A | | 2/2000 | Massonne et al. ......... 549/307 |
| 6,028,204 A | | 2/2000 | Massonne et al. ......... 549/307 |
| 6,229,026 B1 | | 5/2001 | Petersen ..................... 549/467 |
| 6,258,842 B1 | | 7/2001 | Petersen et al. ............ 514/469 |
| 6,291,689 B1 | | 9/2001 | Petersen et al. ............ 549/467 |
| 6,310,222 B1 | | 10/2001 | Ikemoto et al. ............ 549/467 |
| 6,365,747 B1 | | 4/2002 | Dall'Asta et al. .......... 548/146 |
| 6,403,813 B1 | * | 6/2002 | Petersen et al. ............ 549/305 |
| 6,433,196 B1 | | 8/2002 | Ikemoto et al. |
| 6,458,973 B1 | | 10/2002 | Dall'Asta et al. |
| 6,703,516 B2 | | 3/2004 | Dall'Asta et al. |
| 2001/0027256 A1 | | 10/2001 | Peterson et al. ............ 549/462 |
| 2002/0004604 A1 | | 1/2002 | Peterson et al. ............ 549/462 |
| 2002/0019546 A1 | | 2/2002 | Peterson et al. ............ 549/307 |
| 2002/0025982 A1 | | 2/2002 | Peterson et al. ............ 514/469 |
| 2002/0026062 A1 | | 2/2002 | Peterson et al. ............ 549/467 |
| 2002/0028956 A1 | | 3/2002 | Weber ........................ 549/307 |
| 2002/0035277 A1 | | 3/2002 | Rock et al. ................. 549/467 |
| 2002/0040153 A1 | | 4/2002 | Peterson .................... 549/467 |
| 2003/0009038 A1 | | 1/2003 | Dall'Asta et al. |

FOREIGN PATENT DOCUMENTS

| | | | |
|---|---|---|---|
| CA | 2023507 | 2/1991 | ......... C07C/209/84 |
| DE | 26 30 927 | 1/1978 | |
| WO | 2 242 007 | 3/1974 | |
| WO | 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ......... C07D/307/87 |
| WO | 00/39112 | 7/2000 | ......... C07D/307/87 |
| WO | 00/44738 | 8/2000 | ......... C07D/307/88 |
| WO | WO 01/32642 | 5/2001 | |
| WO | WO 01/32643 | 5/2001 | |
| WO | 01/47877 | 7/2001 | |
| WO | 01/66536 | 9/2001 | ......... C07D/307/87 |

OTHER PUBLICATIONS

U.S. Appl. No. 10/012,025, filed Nov. 6, 2001.
U.S. Appl. No. 10/012,054, filed Nov. 6, 2001.
U.S. Appl. No. 10/035,005, filed Dec. 20, 2001.
U.S. Appl. No. 10/046,126, filed Jan. 8, 2002.
Levy, L.F., "4–Aminophthalide and Some Derivatives", *J. Chem. Soc.* pp. 867–870 (1931).
Tirouflet J., "Phtalide Subsitutes en 5", *Bull. Soc. Sci. de Bretagne* 26:35–43 (1951).
Bigler, Allan et al., "Quantitative Structure–activity Relationships in a Series of Selective 5–HT uptake inhibitors," *Eur. J. Med. Chem.* 3:289–295 (1997).
Forney L., "Reaction of Terephthalic Acid with Formaldehyde in Sulfur Trioxide Media," *J. Org. Chem.* 35:1695–1696 (1970).
Dordor et al., "Reaction of Oxazolines with Phosphorus Oxychloride," *Tetrahedron Letters* 24:1437–1440 (1983).
Barton et al., *Comprehensive Organic Chemistry. The Synthesis and Reactions of Organic Compounds*, vol. 2, pp. 1024–1025.
Forney, Leroy et al., "The Reaction of Formaldehyde with Deactivated Benzic Acids. An Ester–Directed Electrophilic Aromatic Substitution Process," *J. Org. Chem.* 36, 5: 689–693 (1971).
Le Blanc, J.R. et al., "Di– and Tetracarboxydiphenyl-methanes and Derivatives," *J. Org. Chem.* 26: 4731–4733 (1961).

(Continued)

*Primary Examiner*—Golam M M Shameem
(74) *Attorney, Agent, or Firm*—Darby & Darby

(57) ABSTRACT

5-carboxyphthalide is obtained with very high purity and in high yields by a convenient process comprising reaction of terephthalic acid

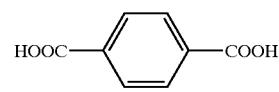

with paraformaldehyde $HO(CH_2)_nH$ in oleum.

16 Claims, No Drawings

OTHER PUBLICATIONS

Bigler, Allan J. et al., "Quantitative structure–activity relationships in a series of selective 5–HT uptake inhibitors," Eur. J. Med. Chem. 12, 3: 289–295 (1977).

Buehler, Calvin A. et al., Survey of Organic Synthesis: 951, New York: John Wiley & Sons, (1970).

* cited by examiner

METHOD FOR THE PREPARATION OF 5-CARBOXYPHTHALIDE

CROSS REFERENCE TO RELATED APPLICATION

This application is a continuation of U.S. patent application Ser. No. 09/690,301, filed Oct. 17, 2000 now U.S. Pat. No. 6,458,973.

The present invention relates to a novel process for the preparation of 5-carboxyphthalide, a starting material for the manufacture of the well-known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a selective serotonin reuptake inhibitor which has successfully been marketed as an antidepressant drug for some years. It has the following structure:

Formula I

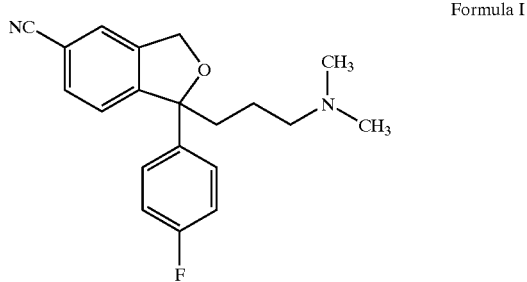

and it may be prepared by the process described in U.S. Pat. No. 4,650,884 according to which 5-cyanophthalide is subjected to two successive Grignard reactions, i.e. with 4-fluorophenyl magnesium halogenide and N,N-dimethylaminopropyl magnesium halogenide, respectively, and the resulting dicarbinol compound is subjected to a ring closure reaction by dehydration. The 5-cyanophthalide may in its turn be obtained by reaction of 5-carboxyphthalide with a dehydrating agent and a sulfonamide of the formula $H_2N—SO_2—R$ wherein R is $NH_2$, alkyloxy, optionally substituted phenyloxy, or substituted phenyl in order to obtain 5-cyanophthalide, cf. our co-pending Danish patent application No. PA199801718.

5-Carboxyphthalide has been described as a useful intermediate in the polymer and paint industry. However, no reliable commercial source is available at present. A known process comprises catalytic hydrogenation of trimellithic acid (DE-A1 2630927). This process provides a mixture of the 5- and 6-carboxyphthalides and, accordingly, it requires elaborate and costly purification. According to J. Org. Chem. 1970, 35, p. 1695-1696, 5-carboxyphthalide is synthesised by reaction of terephthialic acid with trioxanie in liquid $SO_3$. During this process, trioxane sublimates and precipitates thereby obstructing the equipment.

Though a number of other methods failed, it has now been found that 5-carboxyphthalide may be prepared from terephthalic acid in high yields by a convenient, cost-effective procedure.

DESCRIPTION OF THE INVENTION

Accordingly, the present invention provides a process for the manufacture of 5-carboxyphthalide

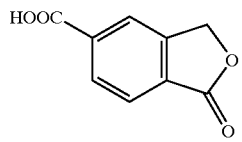

comprising reaction of terephthalic acid

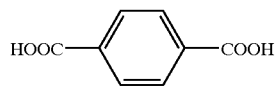

with paraformaldehyde, $HO(CH_2O)_nH$, in oleum.

By the process of the invention, 5-carboxyphtlialide is obtained with very high purity and in high yields (>about 75%). Furthermore, as compared with the prior art process (J. Org. Chem. 1970, 35, p. 1695-1696), the process of the invention takes place without precipitation of sublimated trioxane which obstructs the equipment e.g. by precipitating in condensers.

The oleum used is commercially available oleum. So the following are available from Aldrich/Fluka:

12–17% $SO_3$ (Fuming sulfuric acid) 15% oleum
18–24% $SO_3$ (Fuming sulfuric acid) 20% oleum
27–33% $SO_3$ (Fuming sulfuric acid) 30% oleum
From other sources 20% oleum contains 20–25% $SO_3$ In the method of the invention, the terephthalic acid is condensed with paraformaldehyde liberating water, which reacts with the $SO_3$. When the reaction is complete, 5-carboxyphthalide may be isolated as follows. The reaction mixture is hydrolysed with water. The condensed product, 5-carboxyphthalide inclusive possible diphthalide impurities may then be filtered off, and the 5-carboxyphthalide may be dissolved in aqueous medium by adjusting pH to about 6.7 to 7.3, leaving possible diphthalide impurities in the solid phase The diphthalide present may be filtered off whereupon 5-carboxyphthalide may be precipitated by acidification, filtered off, washed with water and dried.

Preferably 1.0–1.33 equivalents $CH_2O$ and 1.0–2.5, preferably 1.0–2.0 are used. More preferably 1.25–1.5 equivalents $SO_3$ per equivalent terephthalic acid are used. Most preferably, about 1.37 equivalents (corresponding to about 33 kg 20–25% oleum/kg terephthalic acid) are used per equivalent terephthalic acid.

The reaction of terephthalic acid with paraformaldehyde is carried out at elevated temperature, conveniently at about 50–148° C., preferably 115–125° C. or 138–148° C. The reaction time is not critical and may easily be determined by a person skilled in the art, a reaction time of 17–21 hours is preferably used for a 210 kg batch at 115–125° C. The time is decreased with increasing temperature.

The adjustment of pH to 6.3 to 7.3 in order to dissolve the 5-carboxyphthalide formed may be effected by NaOH, e.g. about 10% aqueous NaOH.

Acidification in order to precipitate the 5-carboxyphthalide may be carried out by adding sulphuric acid until pH=2.

The terephthalic acid used as a starting material is commercially available.

EXAMPLES

The invention is father illustrated by the following example.

Example 1

5-Carboxyphthalid

Terephthalic acid (10 kg) is charged into a reactor. Oleum (20% (18–24% $SO_3$); 6 kg/kg terephthalic acid) is added and then paraformaldehyde (1.33 equivalents, 0.24 kg/kg terephthalic acid) is added. The mixture is agitated at 125° C. for 17 hours. Water (13 kg/kg terephthalic acid and filter aid is added, the temperature is adjusted to about 70° C. The precipitate is filtered of, washed with water and suspended in water. The pH of the suspension is adjusted to about 7 with NaOH, activated carbon, 0.07 kg/kg terephthalic acid is added, and then the mixture is filtered, the precipitate is rinsed with water. The temperature of the filtrate is adjusted to about 65° C. and the pH is adjusted to about 2 with 50% sulfuric acid. The 5-carboxyphthalide precipitated is separated by filtration washed and dried. Yield 83%.

Example 2

5-Carboxyphthalid

Oleum (20–25% $SO_3$ 43 kg) is charged into a reactor. Terephthalic acid (13 Kg) and then paraformaldehyde (3.8 Kg) is added. The mixture is agitated at 138–148° C. for 4½ hours. Water (87 L) is added and the temperature is adjusted to about 100° C. The precipitate is filtered of, washed with water and suspended in water. The pH of the suspension is adjusted to about 7 with NaOH (about 10%), activated carbon, 0.5 Kg is added, and then the mixture is filtered, the precipitate is rinsed with water. The temperature of the filtrate is adjusted to about 85° C. and the pH is adjusted to about 2 with 96% sulfuric acid. The 5-carboxyphthalide precipitated is separated by filtration washed and dried. Yield 82%.

What is claimed is:

1. A process for the preparation of 5-carboxyphthalide of formula A

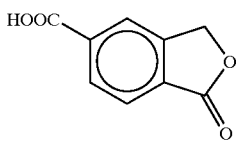

(A)

which comprises forming a mixture by adding formaldehyde and terephthalic acid of formula I

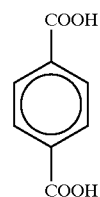

(I)

to fuming sulfuric acid containing at least 18% of $SO_3$, heating the mixture at 50–148° C. and isolating the 5-carboxyphthalide thus obtained.

2. A process according to claim 1, in which the mixture is heated at 138–148° C.

3. A process according to claim 1, in which the mixture is heated at 115–125° C.

4. A process according to claim 1, in which the fuming sulfuric acid contains 18–24% $S_3$.

5. A process according to claim 1, in which the fuming sulfuric acid contains 20–25% $SO_3$.

6. A process according to claim 1, in which the fuming sulfuric acid contains 27–33% $SO_3$.

7. A process according to claim 1, in which formaldehyde is used in form of its precursor paraformaldehyde.

8. A process according to claim 1, in which 5-carboxyphthalide is isolated by neutralization of the reaction mixture with a base.

9. A process according to claim 8, in which said base is an alkaline metal base.

10. A process according to claim 9, in which said alkaline metal base is sodium hydroxide.

11. A process according to claim 1, in which formaldehyde is added to fuming sulfuric acid after the addition of terephthalic acid.

12. A process according to claim 1, in which, at the end of the reaction, the 5-carboxyphthalide is isolated by the formation of a solution containing a salt thereof which is neutralized with an acid.

13. A process according to claim 12, in which said salt is the sodium salt.

14. A process for the synthesis of citalopram, in which a process for the synthesis of 5-carboxyphthalide according to claim 1 is contained.

15. Citalopram which has been produced by a process comprising the process for the synthesis of 5-carboxyphthalide according to claim 1.

16. A process according to claim 1, in which the fuming sulfuric acid contains at least 20% $SO_3$.

* * * * *

UNITED STATES PATENT AND TRADEMARK OFFICE
CERTIFICATE OF CORRECTION

PATENT NO. : 6,888,009 B2
DATED : May 3, 2005
INVENTOR(S) : Hans Petersen et al.

It is certified that error appears in the above-identified patent and that said Letters Patent is hereby corrected as shown below:

<u>Title page,</u>
Item [63], Related U.S. Application Data, please delete "Continuation of application No. 09/690,301, filed on Oct. 17, 2000, now Pat. No. 6,458,973." and substitute with -- This is a division, of application Serial No. 09/692,653, filed October 19, 2000 now Pat. No. 6,403,813 --.

Signed and Sealed this

Second Day of August, 2005

JON W. DUDAS
*Director of the United States Patent and Trademark Office*